United States Patent
Kang et al.

(10) Patent No.: US 12,098,384 B2
(45) Date of Patent: Sep. 24, 2024

(54) ADENOVIRAL VECTOR NOT INCLUDING REPLICATION COMPETENT ADENOVIRUS, AND USE THEREOF

(71) Applicant: CELLID CO., LTD., Seoul (KR)

(72) Inventors: Chang-Yuil Kang, Seoul (KR); Bongju Park, Seoul (KR); Kwang-Soo Shin, Seoul (KR); Tae-Gwon Oh, Seoul (KR)

(73) Assignee: Cellid Co., Ltd., Seoul (KR)

(*) Notice: Subject to any disclaimer, the term of this patent is extended or adjusted under 35 U.S.C. 154(b) by 0 days.

(21) Appl. No.: 18/268,890

(22) PCT Filed: Jan. 20, 2022

(86) PCT No.: PCT/KR2022/001046
§ 371 (c)(1),
(2) Date: Jun. 21, 2023

(87) PCT Pub. No.: WO2022/158879
PCT Pub. Date: Jul. 28, 2022

(65) Prior Publication Data
US 2024/0043871 A1    Feb. 8, 2024

(30) Foreign Application Priority Data
Jan. 21, 2021 (KR) .................. 10-2021-0008666

(51) Int. Cl.
*C12N 15/86* (2006.01)
*C07K 14/165* (2006.01)
*A61K 39/00* (2006.01)

(52) U.S. Cl.
CPC ............ *C12N 15/86* (2013.01); *C07K 14/165* (2013.01); *A61K 2039/5256* (2013.01); *C12N 2710/10022* (2013.01); *C12N 2710/10041* (2013.01); *C12N 2770/20022* (2013.01); *C12N 2770/20034* (2013.01)

(58) Field of Classification Search
CPC ......... C12N 15/86; C12N 2710/10022; C12N 2710/10041; C12N 2770/20022; C12N 2770/20034; A61K 2039/5256
See application file for complete search history.

(56) References Cited

U.S. PATENT DOCUMENTS

| | | | |
|---|---|---|---|
| 6,312,946 B1 | 11/2001 | Yeh et al. | |
| 6,544,780 B1 | 4/2003 | Wang | |
| 7,820,440 B2* | 10/2010 | Vogels ................ | A61P 31/16 435/456 |
| 9,056,090 B2 | 6/2015 | Colloca et al. | |
| 2003/0219410 A1 | 11/2003 | Calatrava | |
| 2004/0106193 A1 | 6/2004 | Kay et al. | |
| 2005/0118139 A1 | 6/2005 | Huang et al. | |
| 2020/0061185 A1 | 2/2020 | Graham et al. | |
| 2021/0139543 A1* | 5/2021 | He ..................... | A61P 31/14 |
| 2022/0305111 A1 | 9/2022 | Zubkova et al. | |
| 2022/0354943 A1* | 11/2022 | Krishnan ............. | A61K 39/12 |
| 2023/0022109 A1 | 1/2023 | Wei et al. | |

FOREIGN PATENT DOCUMENTS

| | | |
|---|---|---|
| CN | 111218459 A | 6/2020 |
| EP | 1427443 A1 | 6/2004 |
| EP | 1470233 A1 | 10/2004 |
| JP | 2000-106875 A | 4/2000 |
| JP | 2019-528072 A | 10/2019 |
| KR | 10-2020-0074988 | 6/2020 |
| RU | 2720614 C1 | 5/2020 |
| WO | WO 2000/77168 A2 | 12/2000 |
| WO | WO 2003/018055 A1 | 3/2003 |
| WO | WO 2003/064666 A1 | 8/2003 |
| WO | WO 2018-037045 A1 | 3/2018 |
| WO | WO 2021/002776 A1 | 1/2021 |

OTHER PUBLICATIONS

McVey D, Zuber M, Ettyreddy D, Reiter CD, Brough DE, Nabel GJ, King CR, Gall JG. Characterization of human adenovirus 35 and derivation of complex vectors. Virol J. Oct. 19, 2010;7:276. (Year: 2010).*
Tauber B, Dobner T. Adenovirus early E4 genes in viral oncogenesis. Oncogene. Nov. 26, 2001;20(54):7847-54. (Year: 2001).*
International Preliminary Report on Patentability in International Application No. PCT/KR2022/001046, issued by the Korean Search Authority of the Korean Intellectual Property Office, completed on Apr. 28, 2023, English translation (4 pages).
International Search Report and Written Opinion in PCT/KR2022/001046, issued by the Korean Search Authority of the Korean Intellectual Property Office, mailed on May 4, 2022, 7 pages (with English translation of the International Search Report, 3 pages).
Koup et al., "Replication-Defective Adenovirus Vectors with Multiple Deletions Do Not Induce Measurable Vector-Specific T Cells in Human Trials," *J Virol.* 83(12): 6318-6322, Jun. 2009.
Mcvey et al., "Characterization of human adenovirus 35 and derivation of complex vectors," *Virol J.* 7: 276, 2010 (15 pages).
Hoffmann et al., "A Multibasic Cleavage Site in the Spike Protein of SARS-CoV-2 Is Essential for Infection of Human Lung Cells," *Molecular Cell* 78, 779-784, May 21, 2020.

(Continued)

*Primary Examiner* — Janet L Andres
*Assistant Examiner* — Ruixue Wang
(74) *Attorney, Agent, or Firm* — Klarquist Sparkman, LLP

(57) ABSTRACT

The present invention relates to a novel adenoviral vector not including a replication competent adenovirus. A recombinant E1/E3/E4-deleted adenoviral vector, of the present invention, in which an antigenic protein and an E4orf6 gene are inserted in an E1 gene-deleted region, has adenovirus productivity, degree of antigen expression, neutralizing antibody production amount, and T cell induction ability that are similar to those of a control group, and thus can be effectively used as a carrier for various vaccines for diseases or anti-cancer vaccines.

14 Claims, 15 Drawing Sheets

Specification includes a Sequence Listing.

(56) References Cited

OTHER PUBLICATIONS

McVey et al., "Characterization of human adenovirus 35 and derivation of complex vectors," *Virology Journal* 2010, 7:276.

Orlando et al., "E4orf6 Variants with Separate Abilities To Augment Adenovirus Replication and Direct Nuclear Localization of the E1B 55-Kilodalton Protein," *Journal of Virology* 76(3):1475-1487, Feb. 2002.

Shtrichman et al., "Adenovirus Type 5 E4 Open Reading Frame 4 Protein Induces Apoptosis in Transformed Cells," *Journal of Virology* 72(4):2975-2982, Apr. 1998.

Tatsis et al., "Adenoviruses as Vaccine Vectors," *Molecular Therapy* 10(4):616-629, E-PUB Aug. 2004.

* cited by examiner

Fig. 11

| Negative control | Positive control | Interference test group#1 | Interference test group#2 |
|---|---|---|---|

RCA Negative test group: $4.14 \times 10^{10}$ VP

| Flask#1 | Flask#2 | Flask#3 | Flask#4 | Flask#5 | Flask#6 | Flask#7 | Flask#8 |
|---|---|---|---|---|---|---|---|
| Flask#9 | Flask#10 | Flask#11 | Flask#12 | Flask#13 | Flask#14 | Flask#15 | Flask#16 |
| Flask#17 | Flask#18 | Flask#19 | Flask#20 | Flask#21 | Flask#22 | Flask#23 | Flask#24 |
| Flask#25 | Flask#26 | Flask#27 | Flask#28 | Flask#29 | Flask#30 | Flask#31 | Flask#32 |
| Flask#33 | Flask#34 | Flask#35 | Flask#36 | | | | |

ADENOVIRAL VECTOR NOT INCLUDING REPLICATION COMPETENT ADENOVIRUS, AND USE THEREOF

CROSS REFERENCE TO RELATED APPLICATIONS

This is the U.S. National Stage of International Application No. PCT/KR2022/001046, filed Jan. 20, 2022, which in turn claims the benefit of Korean Patent Application No. 10-2021-0008666, filed Jan. 21, 2021. The Korean patent application is incorporated herein in its entirety.

SEQUENCE LISTING

The Sequence Listing is submitted as an ASCII text file in the form of the file name "Sequence Listing_2.txt" (2,166,810 bytes), which was created on May 21, 2024, and which is incorporated by reference herein.

BACKGROUND OF THE INVENTION

1. Field of the Invention

The present invention relates to a novel adenoviral vector not including a replication competent adenovirus, and a use thereof.

2. Description of the Related Art

Due to the ability of adenoviruses to achieve highly effective gene delivery and large transgene doses in a variety of target tissues, recombinant adenoviruses have been widely used in gene therapy and vaccine applications.

Adenoviral vectors are theoretically impossible to replicate due to the deletion of the E1 gene, which is essential for replication. However, replication competent adenovirus (RCA) can be created when the E1 gene derived from adenovirus of HEK293 cell line is inserted into the non-replicable adenoviral vector gene through homologous recombination during the production process of the non-replicable adenoviral vector. The presence of RCA in adenoviral vectors leads to a number of safety-related problems, including adenovirus infection, unintended replication of the vector, and worsening inflammatory responses in patients. Regulatory agencies such as KFDA and FDA define RCA-related standards as less than 1 RCA among $3\times10^{10}$ virus particles, and these RCA-related regulations act as an obstacle to mass production of adenoviral vectors.

Methods to overcome the occurrence of RCA largely include the development and manipulation of cell lines for adenovirus proliferation and the manipulation of the adenoviral vector backbone. Specifically, the following strategies are known: 1) a strategy for developing a new cell line introducing only the protein coding portion of the E1 gene region that has no homologous sequence with an adenoviral vector ($1^{st}$ generation adenoviral vector), 2) a strategy to remove the adenovirus genes essential for replication such as E2A, E2B and E4 from the vector and to supplement the protein coding region of the removed gene by introducing it into the cell line ($2^{nd}$ generation adenoviral vector), 3) a strategy to block homologous recombination by removing homologous sequences in HEK293 cell line, 4) a strategy to use other species of adenovirus with less homologous sequences, and 5) a strategy to maintain a non-replicable adenovirus even if it reacquires the E1 gene through homologous recombination.

Two cell lines ($1^{st}$ generation adenoviral vectors) with E1 genes without homologous sequences have been successfully developed and being used commercially. These are the PER.C6 cell line, in which the E1 gene (459-3510 nt) is introduced into human embryonic retinoblasts (HER) cell line, and the N52.E6 (CAP-GT) cell line, in which the E1 gene (505-3522nt) is introduced into primary human amniocytes. However, it is difficult to expect complete resolution of RCA occurrence in the process of multi-passage and mass production with these cell lines. The strategy of supplementing essential genes for replication, such as E2A, E2B and E4, in cell lines ($2^{nd}$ generation adenoviral vector) was heavily studied and developed during 1995-2000, but failed to be commercialized due to low productivity compared to the $1^{st}$ generation adenoviral vectors and unstable expression of the introduced genes. Gene manipulation in HEK293 cell line is difficult due to the complexity of the genome of the 293 cell line and the number of copies of the introduced E1 gene (7 copies), and the use of other species of adenovirus may pose a safety risk to the administrator. Lastly, an adenoviral vector manipulation strategy that prevents the appearance of RCA by limiting the size of the adenovirus genome even if homologous recombination occurs by placing antigen genes in the E3 region is currently only being conducted at the research level.

Accordingly, the present inventors have completed this invention by developing a novel adenoviral vector that has adenovirus productivity and degree of antigen expression similar to those of the existing adenoviral vector without including a replication competent adenovirus even if homologous recombination occurs by deleting the E4 gene essential for adenovirus replication and relocating it to the site of the E1 gene deletion.

SUMMARY OF THE INVENTION

It is an object of the present invention to provide a novel adenoviral vector not including a replication competent adenovirus, and a use thereof.

To achieve the above object, the present invention provides a recombinant adenoviral vector characterized by the insertion of the E4 gene into the deletion site of the E1 gene in the adenovirus in which the E1, E3 and E4 genes have been deleted.

In addition, the present invention provides a vaccine for preventing coronavirus infection, in which a sequence encoding a coronavirus spike protein is inserted into the vector.

Advantageous Effect

The present invention relates to a novel adenoviral vector not including a replication competent adenovirus. A recombinant E1/E3/E4-deleted adenoviral vector, of the present invention, in which an antigenic protein and an E4orf6 gene are inserted in an E1 gene-deleted region, has adenovirus productivity, degree of antigen expression, neutralizing antibody production amount, and T cell induction ability that are similar to those of a control group, and thus can be effectively used as a carrier for various vaccines for diseases or anti-cancer vaccines.

BRIEF DESCRIPTION OF THE DRAWINGS

FIG. 11 is a diagram showing the results of RCA negative test for the E4re #29 adenoviral vector.

DESCRIPTION OF THE PREFERRED EMBODIMENTS

Figure 1:
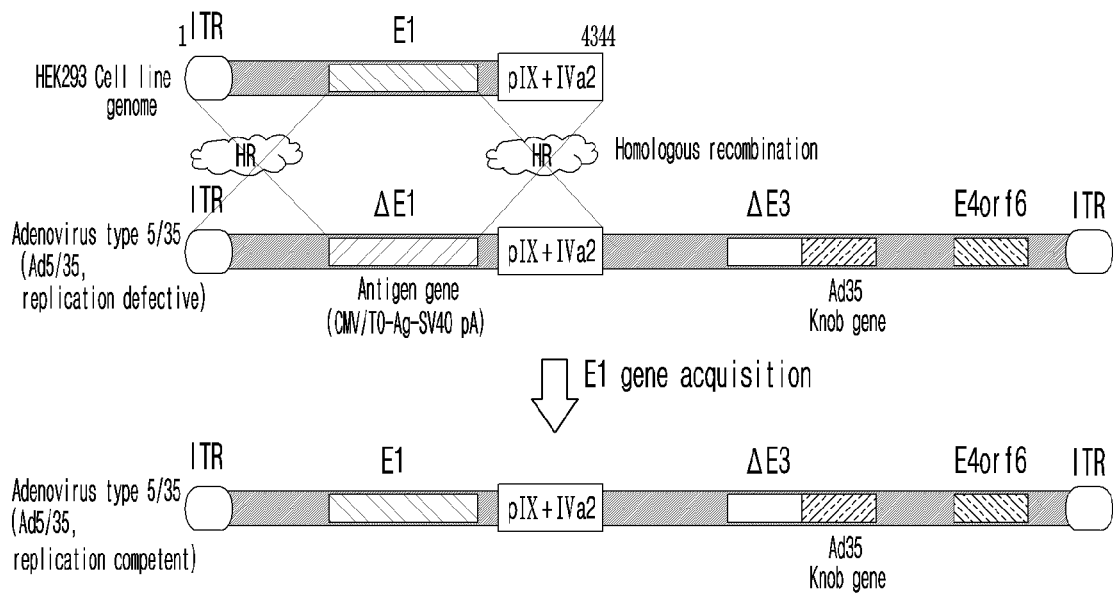
FIG. 1 is a schematic diagram showing the mechanism of replication competent adenovirus generation.
Figure 2:
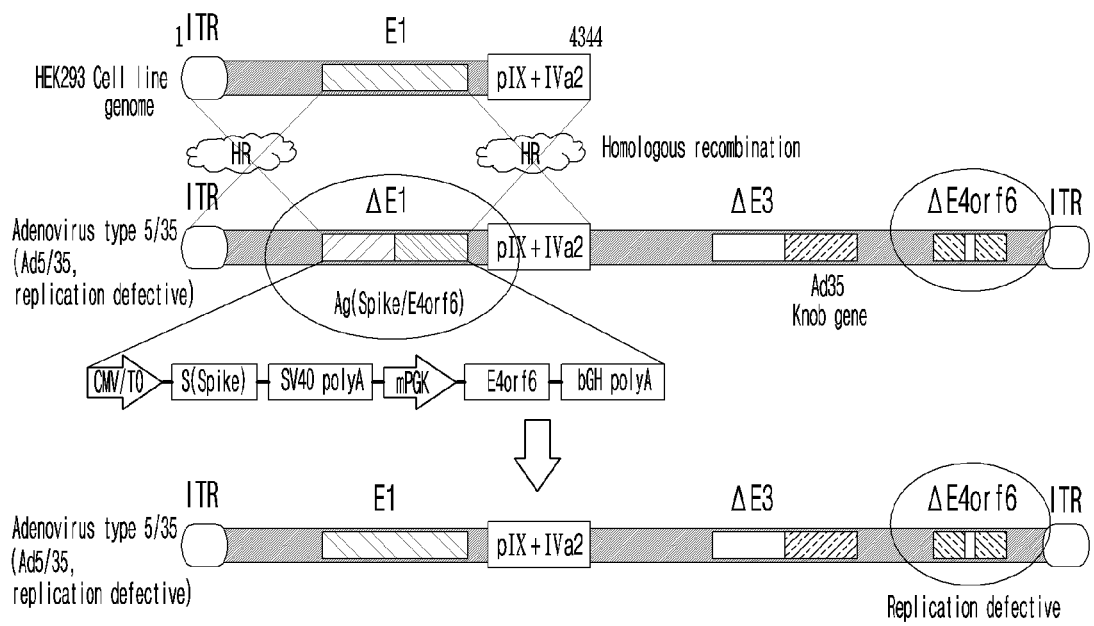
FIG. 2 is a schematic diagram showing the novel adenoviral vector not including a replication competent adenovirus of the present invention.
Figure 3:
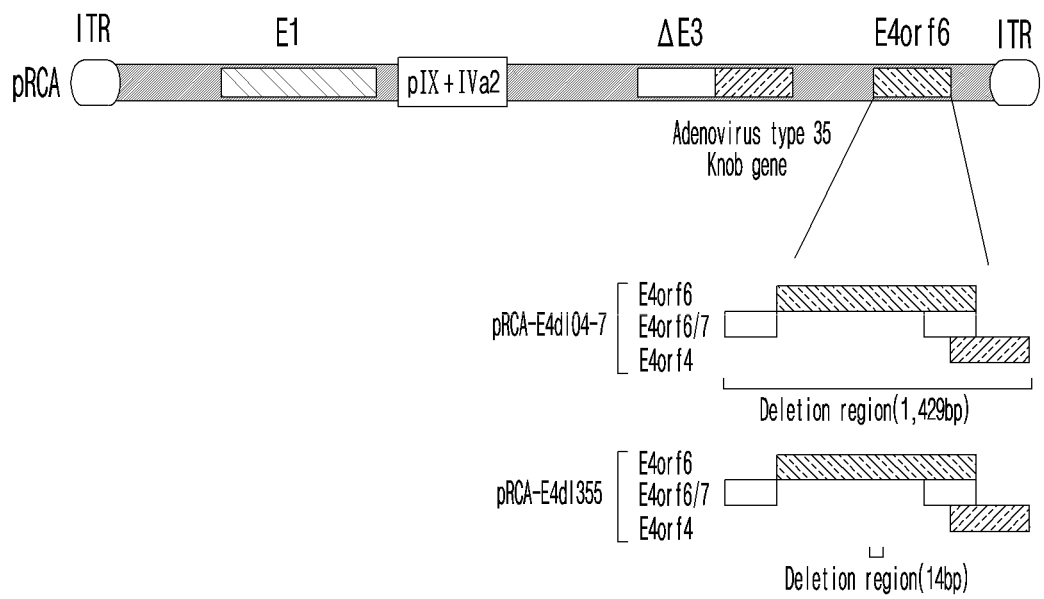
FIG. 3 is a schematic diagram showing the vector with pRCA and 14 bp (pRCA-E4d1355) or 1429 bp (pRCA-E4d104-7) of E4orf6 removed in which a kanamycin resistance gene and a pBR322 origin gene sequence were introduced into a replication competent adenovirus clone in which the E1 gene was acquired by homologous recombination at the E1 deletion site of Ad5/35 in which E1 and E3 of Ad5 were deleted and the knob gene of Ad35 was inserted at the E3 deletion site.

Hereinafter, the present invention is described in detail.

The present invention provides a recombinant adenoviral vector characterized in that the E4 gene is inserted at the deletion site of the E1 gene in the adenovirus in which the E1, E3 and E4 genes are deleted.

In the present invention, "vector" refers to a delivery vehicle that carries a cloned gene (or other fragments of cloned DNA) to a target cell.

The recombinant adenoviral vector has the advantage of being able to use the existing HEK 293 cell line in which the adenovirus E1 gene has been introduced into the genome while minimizing the occurrence of replication competent adenovirus by additionally deleting the E4 gene from the existing E1/E3-deleted adenovirus.

The deleted E4 gene is characterized in that the E4orf6 (E4 open reading frame 6) gene.

The deleted E4 gene is a nucleotide sequence of 10 to 1,000 bp of the E4orf6 gene region, preferably a nucleotide sequence of 10 to 800 bp.

According to a specific embodiment of the present invention, it is preferable to delete a nucleotide sequence having a length of 14 bp or 711 bp of the E4orf6 gene region.

The said adenovirus may be adenovirus serotype 2 (Ad2), adenovirus serotype 4 (Ad4), adenovirus serotype 5 (Ad5), adenovirus serotype 11 (Ad11), adenovirus serotype 26 (Ad26), adenovirus serotype 35 (Ad35), chimpanzee adenovirus serotype 68 (ChAd68), fowl adenovirus serotype 9 (FAd9) or porcine adenovirus serotype 3 (PAd3).

The adenovirus may be a modified form based on Ad5.

The adenovirus may be an adenovirus (Ad5/35) in which the knob gene of adenovirus serotype 5 (Ad5) is replaced with the knob gene of adenovirus serotype 35 (Ad35).

The deleted E4 gene is characterized in that it is a region of E4orf6, E4orf6/7 or E4orf4.

The deleted E4 gene is characterized by a nucleotide sequence having a length of 10 to 1,500 bp, and preferably 14 bp or 1,429 bp.

The E4orf6 gene is characterized in that the kozak sequence is removed.

A sequence encoding an antigen protein may be inserted into the deletion site of the E1 gene.

The sequence encoding the antigen protein can be inserted at the 5' or 3' position of the E4orf6 gene, but preferably at the 5' position of the E4orf6 gene.

The E4orf6 gene may be expressed in a forward direction or in a reverse direction, and preferably in a forward direction.

The E4 gene inserted at the deletion site of the E1 gene is expressed by any one promoter selected from the group consisting of EF-1a, mPGK, RSV, CMV, −0.25 kb of E4orf6, −0.5 kb of E4orf6 and −1.0 kb of E4orf6, but not always limited thereto.

The sequence encoding the antigen protein is characterized in that it is expressed by a cytomegalovirus (CMV) promoter, but not always limited thereto.

The antigen protein may be a spike protein of SARS-COV, MERS-COV or SARS-COV-2.

The antigen protein may be a recombinant spike protein in which a cleavage site between S1 spike protein of SARS-COV, MERS-COV or SARS-CoV-2 and S2 gene is removed and a linker sequence is introduced.

The linker may be characterized in that it is composed of (GGGGS)n (SEQ. ID. NO: 47).

The n is characterized in that it is an integer of 1 to 5.

In addition, the present invention provides a vaccine for preventing coronavirus infection, in which a sequence encoding a coronavirus spike protein is inserted into the recombinant adenoviral vector.

The coronavirus is characterized in that it is SARS-COV, MERS-COV or SARS-COV-2 belonging to Betacoronavirus.

The genome homology between SARS-COV-2 and SARS-COV is as high as 79.6%, and the genome homology between SARS-COV-2 and MERS-COV is as high as 50%. In particular, SARS-COV-2 and MERS-COV have a similar homology (35%) of a spike protein, which is the target of the present invention, while SARS-COV-2 and SARS-COV have a very high spike protein homology (76%).

The spike protein is characterized in that it is a recombinant spike protein in which a cleavage site between S1 spike protein and S2 gene is removed and a linker sequence is introduced.

In vaccines, it is important that antigens are secreted in large amounts, but even if they are expressed in large amounts, if they are initially degraded, they do not stimulate immune cells to sufficiently induce an immune response, so it is very important that the expressed antigens have high stability. The recombinant spike protein of the present invention in which S1 and S2 are linked by a linker sequence has a high degree of antigen expression and improved stability, and thus has excellent ability to generate neutralizing antibodies and induce T cell reactivity.

The term "immune response" may include humoral and cellular immune responses, such as CD4+ or CD8+ cell activation, but not always limited thereto.

The spike protein (S protein) covers the surface of a coronavirus particle and is a spike-shaped protein used when the coronavirus invades human cells and is composed of S1 and S2 subunits. The spike protein infects the human body by binding to angiotensin converting enzyme 2 (ACE-2) receptor of the human cell, penetrating into the cell and pushing the genetic material (RNA) to replicate the genetic material itself.

The recombinant protein is characterized in that a cleavage site between the S1 and S2 genes, which are subunits of the spike protein, has been removed.

The protein is characterized in that a cleavage site between the S1 and S2 genes is removed and linked by a linker sequence.

The linker is characterized in that it is composed of (GGGGS)n (SEQ. ID. NO: 47), wherein n is an integer of 1 to 5.

The domains constituting each protein have a distance (linker sequence length) optimized for interaction according to their unique characteristics, and the structural stability of the protein is exhibited according to the length of the linker sequence. Therefore, n in the protein may preferably be 1 or 3, most preferably n is 1.

If n exceeds 4, a number of repetitive sequences are generated, and the linker sequence may be deleted by unintentional homologous recombination, and the stability of the protein may be reduced.

The spike protein antigen linked by the linker sequence is characterized by increased stability.

In a specific embodiment of the present invention, a replication competent adenovirus that reacquired the E1 gene, which was generated during the production of adenovirus type 5/35 (Ad5/35) in which part of the E4 gene was deleted, exhibited replication incompetence. Even when the E1 gene was acquired by homologous recombination, it was confirmed that adenovirus replication did not occur when the E4orf6 gene was deleted (see FIG. 4). A recombinant adenoviral vector in which the antigen protein and E4orf6 gene were inserted into the deletion site of the E1 gene according to i) the number of nucleotide sequences of the deleted E4, and ii) the order and direction of insertion of the antigen protein and E4orf6 gene was constructed, and adenovirus productivity was evaluated. As a result, it was confirmed that the vectors (E4re #1 and E4re #11) in which 14 bp of E4orf6 was deleted, the antigen protein was ligated to the 5' position of the rearranged E4orf6, and the rearranged E4orf6 was expressed forwardly had high adenovirus productivity (Table 2).

Recombinant adenoviral vectors with a different type of promoter for expressing the E4orf6 rearranged in the E4re #1 and E4re #11 vectors were constructed, and adenovirus productivity was evaluated. As a result, 5 types of vectors with increased productivity (E4re #13, E4re #14, E4re #18, E4re #19 and E4re #20) were confirmed (Table 3).

Productivity was repeatedly tested for 7 vectors that were evaluated to have excellent productivity (E4re #1, E4re #11, E4re #13, E4re #14, E4re #18, E4re #19 and E4re #20). As a result, 5 types of vectors with similar productivity to the control vector (E4re #13, E4re #14, E4re #18, E4re #19 and E4re #20) were confirmed (Table 4).

Among the 4 vectors excluding the E4re #18 with the potential to compromise genetic stability (E4re #13, E4re #14, E4re #19 and E4re #20) from which the −12, 27, 42, 57, 318, 421, and 711 bp sequences from the C-terminal region of the E4orf6 coding region were removed, the E4re #29 vector, in which the 711 sequence of E4orf6 was removed and the E4re #13 antigen was introduced, showed high adenovirus productivity.

Viral stock solution productivity was evaluated in 5 vectors (E4re #13, E4re #14, E4re #19, E4re #20 and E4re #29). As a result, the productivity was 73 to 98% compared to the control group (Table 6). A cell-based RCA negative test was performed with the E4re #29 adenoviral vector. As a result, replication competent adenovirus (RCA) was not detected (FIG. 11), and it was confirmed that RCA was not detected even when the virus passage increased (FIG. 12). In addition, the intracellular degree of antigen expression was evaluated for 6 vectors (E4re #1, E4re #13, E4re #14, E4re #19, E4re #20 and E4re #29). As a result, it was confirmed that the E4re #13 and E4re #29 vectors had the highest intracellular degree of antigen expression (FIGS. 13A to 13C), and the neutralizing antibody production amount in 5 vectors (E4re #1, E4re #13, E4re #14, E4re #20 and E4re #29) was the same as that of the control group (FIGS. 14A to 14H).

Therefore, the recombinant adenoviral vector of the present invention can be effectively used as a carrier for various vaccines for diseases or anti-cancer vaccines.

Hereinafter, the present invention will be described in detail by the following examples and experimental examples.

However, the following examples and experimental examples are only for illustrating the present invention, and the contents of the present invention are not limited thereto.

Example 1: Construction of Replication Competent Adenovirus (RCA) Vector and E4orf6-Deleted Adenoviral Vector (pRCA-E4d1355 and pRCA-E4d104-7)

A replication competent adenovirus (RCA) clone that reacquired the E1 gene, which was generated during the production of adenovirus type 5/35 (Ad5/35) was secured, and a pRCA (SEQ. ID. NO: 1, 36,262 bp) adenoviral vector was constructed by introducing a kanamycin resistance gene and a pBR322 origin gene sequence. The pRCA is a form in which the E3 gene is deleted based on adenovirus serotype 5 (Ad5), and a fiber, which is a cell receptor binding site, is substituted with a fiber of adenovirus serotype 35 (Ad35).

A part of the reverse coding sequence of the E4orf6 gene of the pRCA vector was cut using CRISPR/Cas enzyme and sequence and ligation independent cloning (SLIC) technique to construct a pRCA-E4d1355 (SEQ. ID. NO: 2) (E4orf6 deletion site: 33,918-33,931, 14 bp removed) vector. In addition, a pRCA-E4d104-7 (SEQ. ID. NO: 3) (E4 deletion site: 33,238-34,666, 1,429 bp removed) vector in which the entire E4orf6 coding sequence and E4orf4/E4orf6/7, which share a part of the E4orf6 coding sequence, were additionally deleted, was also constructed.

Example 2: Confirmation of Replication Defectiveness of E4orf6-Deleted Adenoviral Vector The control vector pRCA and the E4-deleted vectors pRCA-E4d1355 and pRCA-E4d104-7 were produced using AD-293 cell line, and it was confirmed whether the E4 gene-deleted adenovirus was replication-defective.

Specifically, the AD-293 cell line, about 80% full on a T25 flask, was transformed with 8 μg of each vector along with 20 μl of Lipofectamine 2000 (ThermoFisher, Cat. #: 11668027) to produce an initial adenoviral vector. Two days after the transformation, the cells were divided into two T75 flasks and cultured from 6 days to 14 days after the transformation. When observed under a microscope, if cytopathic effect (CPE) was seen in more than 80% of the cells, it was considered that adenovirus was sufficiently produced and the cells were harvested. If the cytopathic effect was not seen until the 14$^{th}$ day of the transformation, the cells were detached using trypsin and harvested. The harvested cells were disrupted by repeating the process of freezing and thawing in a deep freezer and a 37° C.-water bath incubator three times, which was centrifuged to obtain a supernatant containing adenovirus. For adenovirus amplification, 4×10$^6$ AD-293 cells were distributed in a T175 flask and cultured for two days. Two days later, the supernatant containing each adenovirus was infected by 2 ml per T175 flask and further cultured for 48 hours. After observing the cytopathic effect under a microscope, the cells were harvested and disrupted, and centrifuged to obtain a supernatant containing adenovirus. The viral genome was extracted from some of the supernatant by referring to the High Pure Viral Nucleic Acid Kit (Roche) protocol. The amplified virus copy number was confirmed using a primer specific to Ad35 fiber, a cell receptor binding site present in the pRCA vector.

Figure 4:
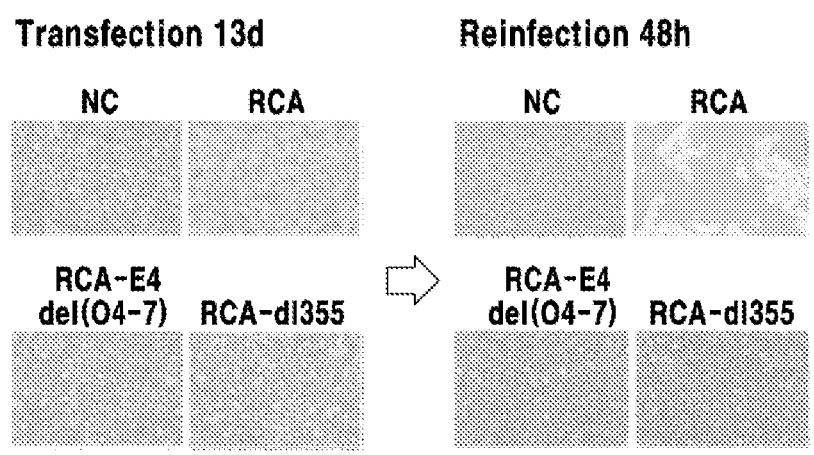
FIG. 4 is a diagram confirming that adenovirus productivity was maintained because no cell lesion effect was observed in the pRCA-E4d1355 in which part of the E4 gene was deleted and the pRCA-E4d104-7 vector in which all of the E4orf4, E4orf6 and E4orf6/7 genes were deleted.
Figure 5:
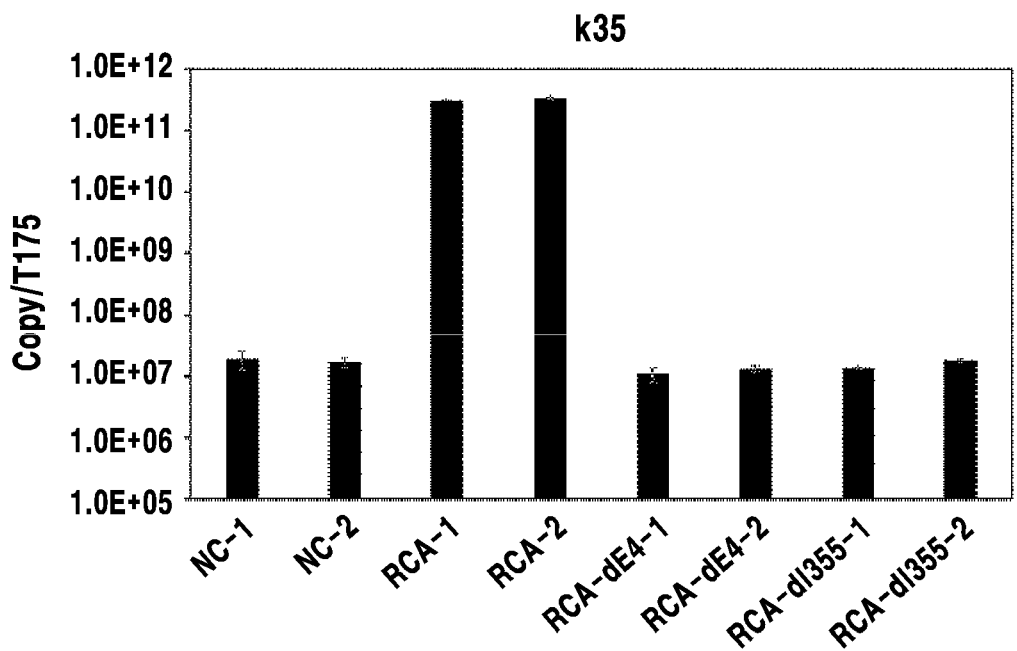
FIG. 5 is a diagram confirming that the adenovirus gene replication did not occur in the pRCA-E4d1355 in which part of the E4 gene was deleted and the pRCA-E4d104-7 vector in which all of the E4orf4, E4orf6 and E4orf6/7 genes were deleted.

As a result, as shown in FIG. 4, the pRCA-E4d1355 with partial deletion of the E4 gene and the pRCA-E4d104-7 with deletion of all the E4orf4, E4orf6 and E4orf6/7 genes showed no cytopathic effect during the two passages of adenovirus production. As shown in FIG. 5, adenoviral gene replication also did not occur in the above vectors. These results suggest that even if the E1 gene is reacquired by homologous recombination, adenovirus replication does not occur when the E4orf6 gene is deleted.

Example 3: Construction of Adenoviral Vector with Rearranged E4 Gene

<3-1>E1 Gene Deletion and Restriction Enzyme Sequence Insertion

The E1 gene of the replication-defective pRCA-E4d1355 and pRCA-E4d104-7 vectors was removed, and the SwaI restriction enzyme site for rearrangement of the E4 gene was inserted.

Figure 6:
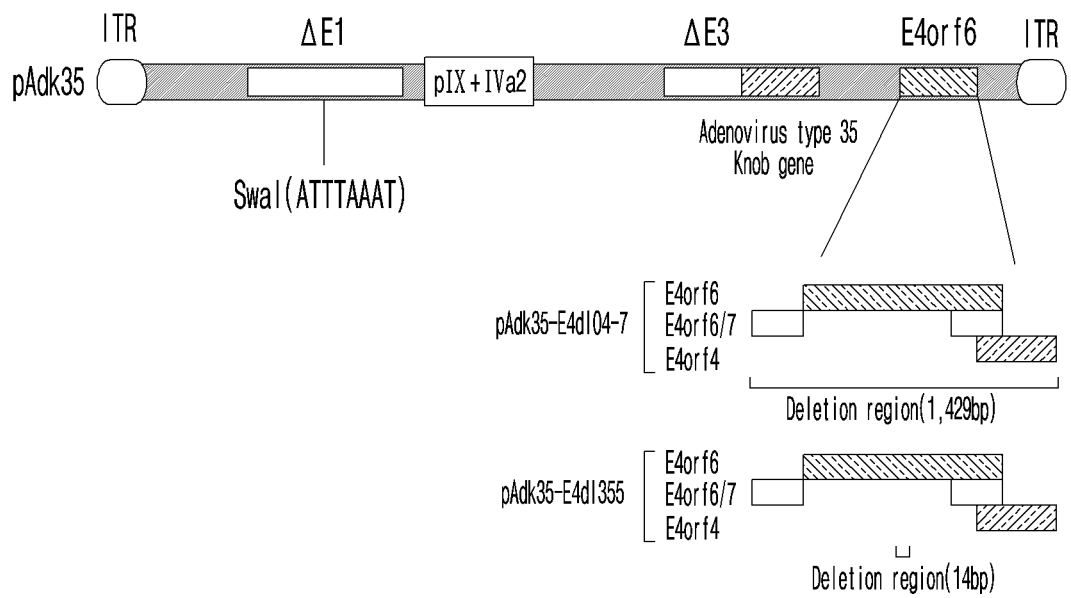
FIG. 6 is a schematic diagram showing the pAdk35-E4d1355 and pAdk35-E4d104-7 vectors in which the E1 gene was deleted and a SwaI restriction enzyme target sequence was inserted therein.

As shown in FIG. 6, site-directed mutagenesis by PCR and in-fusion cloning ligation (Clontech, Cat. #: 639648) were used to construct pAdk35-E4d1355 (SEQ. ID. NO: 4) and pAdk35-E4d104-7 (SEQ. ID. NO: 5) vectors in which the E1 gene was removed and the SwaI restriction enzyme target sequence was inserted therein.

Specifically, the regions were amplified using a primer set that binds to the NheI restriction enzyme site in the fiber gene and the front region of the E1 gene, and a primer set that binds to the NheI restriction enzyme site between the pTP and 52K genes and behind the E1 gene. A SwaI restriction enzyme target sequence was added to the primer that binds to the front and back of the E1 gene, and both ends of the PCP products were overlapped with a 15 bp sequence. An intermediate vector in which the E1 gene was removed and the SwaI restriction enzyme target sequence was inserted therein was constructed by infusion cloning ligation using the two PCR products. The intermediate vector was linearized with NheI restriction enzyme, the remaining adenoviral vector region was amplified by PCR, and pAdk35-E4d1355 (SEQ. ID. NO: 4) and pAdk35-E4d104-7 (SEQ. ID. NO: 5) vectors were constructed by infusion ligation cloning using the two linearized vectors.

<3-2>Construction of Shuttle Vector for E4 Gene Rearrangement and Antigen (Spike) Gene Introduction and Adenoviral Vector with Rearranged E4

Vectors that introduced E4orf6 and antigen genes in the area where the E1 gene of the replication-defective pRCA-E4d1355 and pRCA-E4d104-7 vectors was removed were constructed as follows.

Specifically, pSBbi-Pur was used as a shuttle vector, and an E4orf6 gene expression cassette and an antigen gene expression cassette were sequentially introduced. As an antigen, a nucleotide sequence encoding a protein obtained by replacing the cleavage site between S1 and S2 of the SARS-COV-2 spike protein with a linker sequence (GGGGS) (SEQ. ID. NO: 47) was used.

Figure 7:
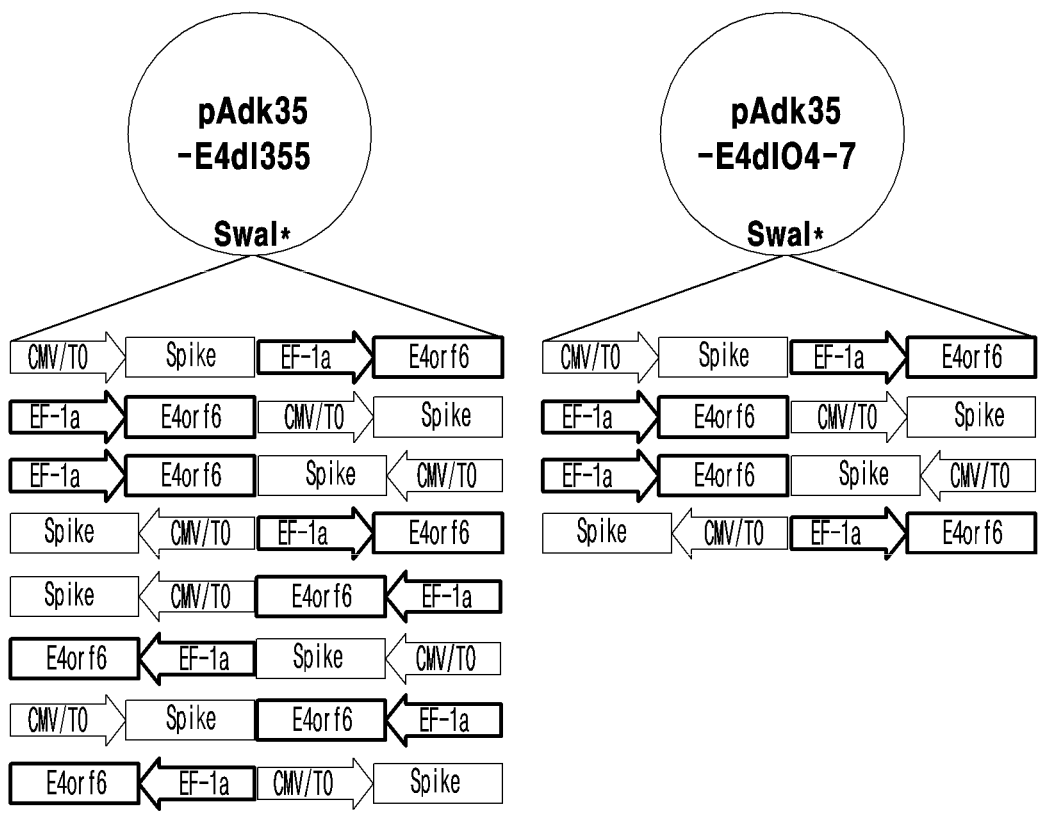
FIG. 7 is a schematic diagram showing the 12 kinds of adenoviral vectors expressing a spike protein antigen and having the E4orf6 gene rearranged at the E1 deletion site.
Figure 8:
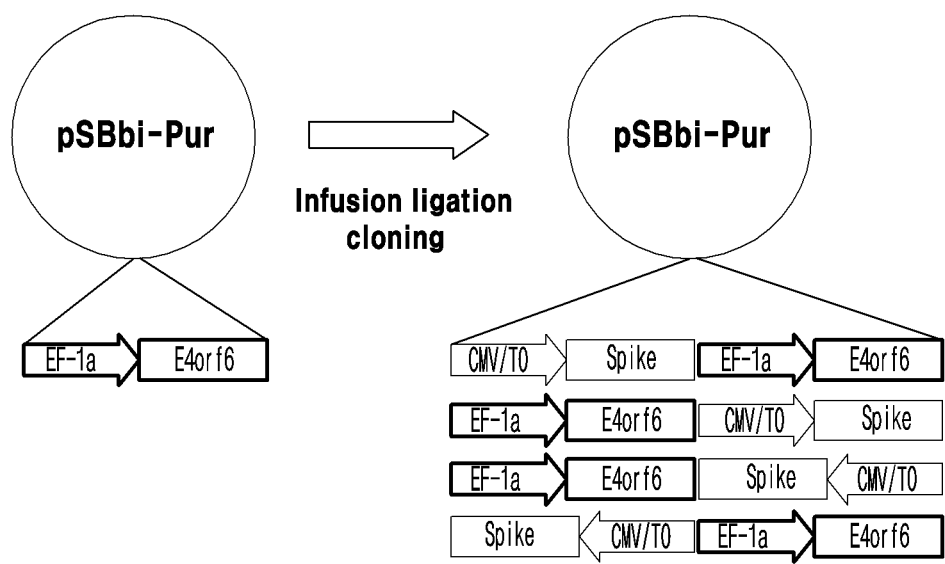
FIG. 8 is a schematic diagram showing the construction process of an adenoviral vector expressing a spike protein antigen and having the E4orf6 gene rearranged at the E1 deletion site.

The entire E4orf6 region of the pRCA vector was amplified by PCR and inserted between the EF-1a promoter and the bGH polyA sequence of the pSBbi-Pur vector by infusion ligation cloning to construct pSBbi-E4orf6 vector. Four types of shuttle vectors were constructed by inserting an antigen (spike protein) expression cassette in the forward and reverse directions at the front of the EF-1a sequence and at the rear of the bGH poly of the pSBbi-E4orf6 vector using site-directed mutagenesis and in-fusion cloning ligation. The antigen (spike protein) expression cassette sequentially contains a CMV promoter, a tetracycline operator (Tet O), a spike protein antigen, and a SV40 poly A sequence. After amplification using a primer set for amplifying the Spike/E4orf6 expression cassette, 12 adenoviral vectors expressing the spike protein antigen in which the E4orf6 gene was relocated to the E1-deleted region were constructed by infusion cloning ligation with the pAdk35-E4d1355 and pAdk35-E4d1O4-7 vectors digested with SwaI, as shown in FIG. 7. The differences between the 12 vectors are as follows: 1) E4-deleted region (14 bp deletion or 1.429 bp deletion of E4orf6, 2) location of spike protein and E4orf6 gene (spike protein and E4orf6 or E4orf6 and spike protein), and 3) directionality (forward or reverse).

TABLE 1

| Abbreviation | Full name | SEQ. ID. NO |
|---|---|---|
| 4re#1 | Adk35F2-Spike/E4orf6-E4dl355 | SEQ. ID. NO: 6 |
| 4re#2 | Adk35R2-Spike/E4orf6-E4dl355 | SEQ. ID. NO: 7 |
| 4re#3 | Adk35F2-E4orf6/Spike-E4dl355 | SEQ. ID. NO: 8 |
| 4re#4 | Adk35R2-E4orf6/Spike-E4dl355 | SEQ. ID. NO: 9 |
| 4re#5 | Adk35F2-Spike/E4orf6-E4dlO4-7 | SEQ. ID. NO: 10 |
| 4re#6 | Adk35R2-Spike/E4orf6-E4dlO4-7 | SEQ. ID. NO: 11 |
| 4re#7 | Adk35F2-E4orf6/Spike-E4dlO4-7 | SEQ. ID. NO: 12 |
| 4re#8 | Adk35R2-E4orf6/Spike-E4dlO4-7 | SEQ. ID. NO: 13 |
| 4re#9 | Adk35FR-Spike/E4orf6-E4dl355 | SEQ. ID. NO: 14 |
| 4re#10 | Adk35FR-E4orf6/Spike-E4dl355 | SEQ. ID. NO: 15 |
| 4re#11 | Adk35RF-Spike/E4orf6-E4dl355 | SEQ. ID. NO: 16 |
| 4re#12 | Adk35RF-E4orf6/Spike-E4dl355 | SEQ. ID. NO: 17 |

Example 4: Measurement of Adenovirus Productivity of 12 Vectors with Rearranged E4 Gene The adenovirus productivity of the 12 vectors with rearranged E4 gene shown in Table 1 was verified using the 293R cell line.

Specifically, the 293R cell line, about 80% full on a T175 flask, was transformed with 50 µg of each vector along with 100 µl of Lipofectamine 2000 (ThermoFisher, Cat. #: 11668027) to produce an initial adenoviral vector. Two days after the transformation, the cells were divided into four T175 flasks and cultured from 6 days to 14 days after the transformation. When observed under a microscope, if cytopathic effect (CPE) was seen in more than 80% of the cells, it was considered that adenovirus was sufficiently produced and the cells were harvested. If the cytopathic effect was not seen until the 14th day of the transformation, it was determined that the virus productivity was low.

As a result, as shown in Table 2, it was confirmed that adenovirus was sufficiently produced by the E4re #1 and E4re #11 vectors. The E4re #1 and E4re #11 vectors have the following characteristics: 1) they use a backbone of the pAdk35-E4dl355 vector, 2) the rearranged E4orf6 is located behind the antigen gene (spike protein), and 3) they are expressed in the forward direction.

TABLE 2

| Abbreviation | Full name | Cytopathic effect (Full CPE) | Cytopathic effect (CPE) on day 14 |
|---|---|---|---|
| E4re#1 | pAdk35F2-Spike/E4orf6-E4dl355 | 10 | N/A |
| E4re#2 | Adk35R2-Spike/E4orf6-E4dl355 | N/A | 70% |
| E4re#3 | Adk35F2-E4orf6/Spike-E4dl355 | N/A | <1% |
| E4re#4 | Adk35R2-E4orf6/Spike-E4dl355 | N/A | <1% |
| E4re#5 | Adk35F2-Spike/E4orf6-E4dlO4-7 | N/A | 60% |
| E4re#6 | Adk35R2-Spike/E4orf6-E4dlO4-7 | N/A | 10% |
| E4re#7 | Adk35F2-E4orf6/Spike-E4dlO4-7 | N/A | <1% |
| E4re#8 | Adk35R2-E4orf6/Spike-E4dlO4-7 | N/A | <1% |
| E4re#9 | Adk35FR-Spike/E4orf6-E4dl355 | N/A | <3% |
| E4re#10 | Adk35FR-E4orf6/Spike-E4dl355 | N/A | <3% |
| E4re#11 | Adk35RF-Spike/E4orf6-E4dl355 | 10 | <3% |
| E4re#12 | Adk35RF-E4orf6/Spike-E4dl355 | N/A | <3% |

Example 5: Construction of Vector with Rearranged E4 Gene Containing Modified E4 Gene Promoter According to the results of Example 4, the cytopathic effect of the pAdk35-Spike expression vector reaches 90% after 6 to 7 days of transformation. On the other hand, the cytopathic effect of the E4re #1 and E4re #11 vectors reached 90% on day 10 of transformation. These results indicate that the adenoviral genome replication and assembly efficiency of the vector is low or the assembly speed is slow. Since the E4orf6 gene rearranged in the above 12 vectors is expressed by a powerful promoter called EF-1a, unnecessarily strong E4orf6 gene expression may affect the expression of other adenovirus replication-related genes, reducing the efficiency of the overall replication and assembly process. Therefore, the promoter of the E4orf6 gene rearranged in E4re #1 was changed to control the expression level of E4orf6, thereby increasing the replication and assembly efficiency of the adenovirus genome.

Figure 9:
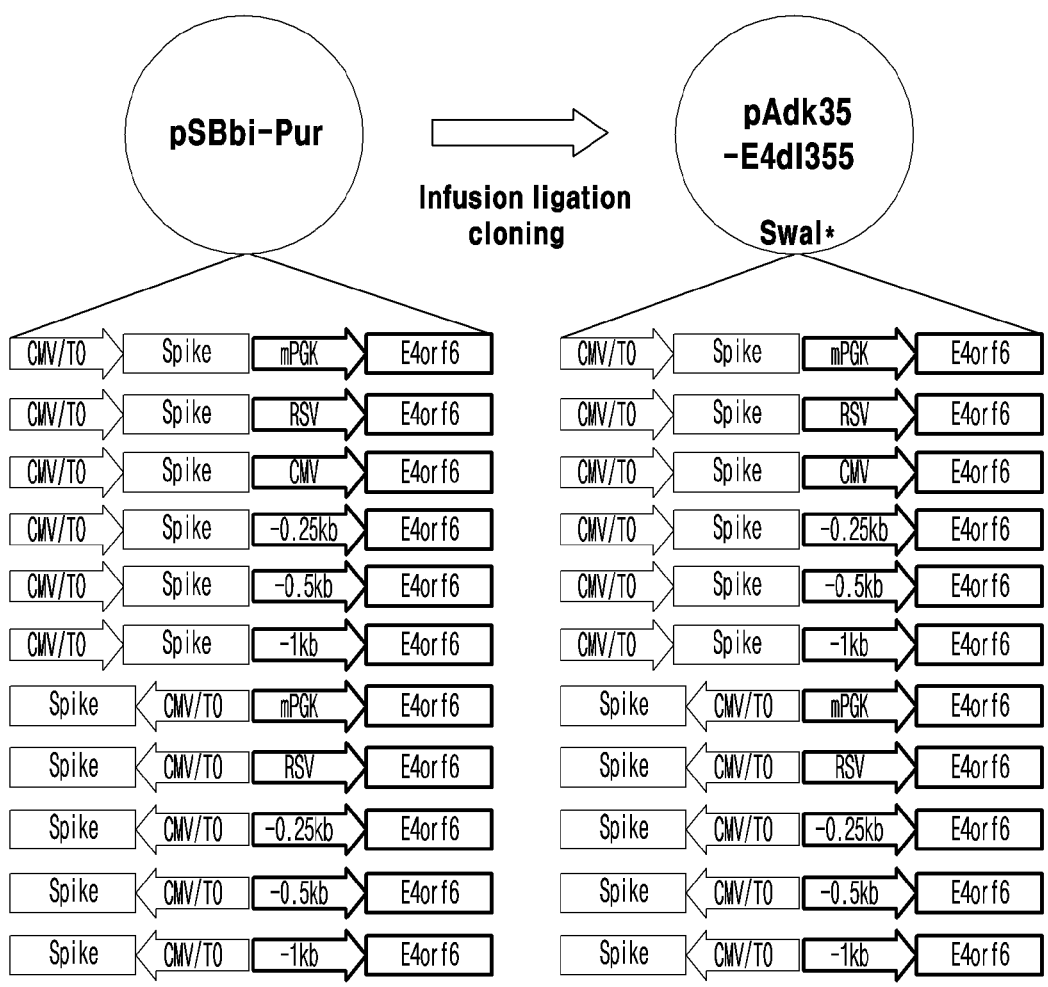
FIG. 9 is a schematic diagram showing the 11 kinds of E4-relocated vectors (E4re #13 to 24) in which the promoter of the relocated E4orf6 gene of E4re #1 and E4re #11 was changed.

Specifically, the EF-1a promoter of the shuttle vector containing the Spike/E4orf6 expression cassettes of E4re #1 and E4re #11 was removed using a site-directed mutagenesis technique. PCR-amplified mPGK, RSV and CMV promoters, and predicted regions of E4orf6-0.25 kb, –0.5 kb and –1 kb promoters were introduced into the shuttle vector from which the EF-1a promoter was removed, by in-fusion cloning ligation, respectively. Finally, 11 shuttle vectors with replaced promoters were constructed, and 11 vectors with rearranged E4 (E4re #13 to 24) were constructed by amplifying the Spike/E4orf6 expression cassette and introducing the same into the pAdk35-E4dl355 vector linearized with SwaI as shown in Table 3 and FIG. 9.

The cytopathic effect of the vectors with rearranged E4 was observed using the 293R cell line, and the productivity was investigated. As a result, it was confirmed that the cytopathic effect of the vector in which the promoter was replaced with the mPGK, RSV, or CMV promoter was advanced by about 2 days.

TABLE 3

| Abbreviation | Full name | SEQ. ID. NO | Cytopathic effect (Full CPE) | Cytopathic effect(CPE) on day 14 |
|---|---|---|---|---|
| E4re#13 | pAdk35F2-Spike/E4orf6(mPGK)-E4dl355 | SEQ. ID. NO: 18 | 8 | N/A |
| E4re#14 | pAdk35F2-Spike/E4orf6(RSV)-E4dl355 | SEQ. ID. NO: 19 | 8 | N/A |
| E4re#15 | pAdk35F2-Spike/E4orf6(−0.25 kb)-E4dl355 | SEQ. ID. NO: 20 | N/A | 50% |
| E4re#16 | pAdk35F2-Spike/E4orf6(−0.5 kb)-pE4dl355 | SEQ. ID. NO: 21 | N/A | 50% |
| E4re#17 | pAdk35F2-Spike/E4orf6(−1 kb)-E4dlO4-7 | SEQ. ID. NO: 22 | N/A | 50% |
| E4re#18 | pAdk35F2-Spike/E4orf6(CMV)-E4dlO4-7 | SEQ. ID. NO: 23 | 8 | N/A |
| E4re#19 | pAdk35RF-Spike/E4orf6(mPGK)-E4dl355 | SEQ. ID. NO: 24 | 8 | N/A |
| E4re#20 | pAdk35RF-Spike/E4orf6(RSV)-E4dl355 | SEQ. ID. NO: 25 | 8 | N/A |
| E4re#21 | pAdk35RF-Spike/E4orf6(−0.25 kb)-E4dl355 | SEQ. ID. NO: 26 | N/A | 70% |
| E4re#22 | pAdk35RF-Spike/E4orf6(−0.5 kb)-E4dl355 | SEQ. ID. NO: 27 | N/A | 50% |
| E4re#23 | pAdk35RF-Spike/E4orf6(−1 kb)-E4dl355 | SEQ. ID. NO: 28 | N/A | 50% |

Example 6: Comparison of Productivity of Vectors with Cytopathic Effect Observed within 14 Days Cells were transformed with 12.5 μg of each vector in a T25 flask using 7 vectors (E4re #1, 11, 13, 14, 18, 19 and 20) whose cytopathic effect was observed within 14 days in the 293R cell line, and the productivity was compared.

Specifically, when the cytopathic effect of the 293R cell line reached 90% or more, the cells were harvested and disrupted to obtain the virus. 2 ml of the obtained virus was reinfected into 293R cells in the size of one T175 flask and cultured for two days. After harvesting and disrupting the cells, the viral genome was extracted, and the copy number of the viral genome was calculated using k35-specific primers and multiplied by 0.7 to calculate the particle number of each virus produced in the T175 flask. The relative production was compared using pAdk35-Spike as a control vector.

As a result, as shown in Table 4, E4re #1 and E4re #11 showed about 45% of the production of the control vector, and the remaining 5 vectors (E4re #13, 14, 18, 19 and 20) showed productions of 83% to 109% of the control vector. It was confirmed that the 5 vectors showed 79% to 99% productivity similar to that of the control vector through repeated experiments.

TABLE 4

| Batch | Virus | Conc. (μg/μℓ) | Average cycle threshold (Cq) | Total virus particle (VP) | Relative % |
|---|---|---|---|---|---|
| #1 | Control | 0.110 | 14.8 | 5.69E+12 | 100% |
| | E4re#1 | 0.104 | 15.7 | 2.64E+12 | 46% |
| | E4re#11 | 0.104 | 15.7 | 2.52E+12 | 44% |
| | E4re#13 | 0.089 | 14.8 | 4.71E+12 | 83% |
| | E4re#14 | 0.099 | 14.6 | 5.73E+12 | 101% |
| | E4re#18 | 0.095 | 14.5 | 6.19E+12 | 109% |
| | E4re#19 | 0.085 | 14.7 | 4.79E+12 | 84% |
| | E4re#20 | 0.098 | 14.7 | 5.26E+12 | 92% |
| #2 | CLA-04 | 0.089 | 14.8 | 4.49E+12 | 100% |
| | E4re#13 | 0.085 | 14.8 | 4.43E+12 | 99% |
| | E4re#14 | 0.074 | 14.6 | 4.35E+12 | 97% |
| | E4re#18 | 0.074 | 14.7 | 4.07E+12 | 91% |
| | E4re#19 | 0.065 | 14.7 | 3.54E+12 | 79% |
| | E4re#20 | 0.065 | 14.7 | 3.57E+12 | 79% |

Example 7: Optimization Process to Minimize RCA Appearance and Maintain Productivity Among the final five vectors (E4re #13, 14, 18, 19 and 20), E4re #18 uses the CMV promoter to express both the gene expressing the spike protein and the E4orf6 rearrangement gene. This may act as a factor that inhibits genetic stability when adenovirus is produced on a large scale by subculture several times, and thus the vector was excluded from the candidate vectors.

In addition, the pAdk35-E4dl355 vector backbone is excellent in terms of productivity, but the E4-deleted region is a sequence consisting of 14 nucleotides in the middle, and there are two homologous sequence regions with the normal E4orf6 gene rearranged in the E1-deleted region. In the course of virus proliferation, homologous recombination within or between vectors may occur, resulting in the recovery of the E4-deleted region and the appearance of RCA. Therefore, an optimization process for minimizing the possibility of RCA appearance and maximally maintaining productivity by changing the E4-deleted region to the C-terminal site from the middle sequence consisting of 14 nucleotides was performed as follows.

Figure 10:
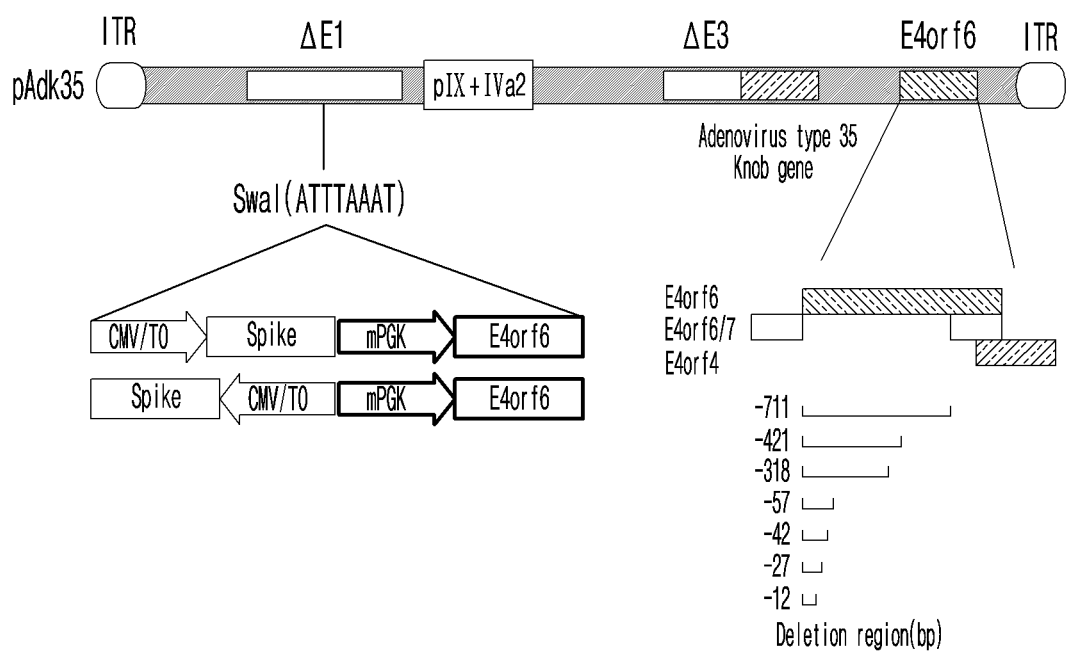
FIG. 10 is a schematic diagram showing the vector in which the antigen F2-Spike/E4orf6 (mPGK) or RF-Spike/E4orf6 (RSV) used in the E4re #13 or 20 vector was introduced into the E1 deletion site, and −12, 27, 42, 57, 318, 421 or 711 bp sequence from the C-terminal region of the E4orf6 coding region were removed.

Specifically, as shown in FIG. 10, sequences of −12, 27, 42, 57, 318, 421, and 711 bp from the C-terminal region of the E4orf6 coding region were removed. In addition, the antigens F2-Spike/E4orf6 (mPGK) and RF-Spike/E4orf6 (RSV) used in the E4re #13 and 20 vectors were introduced into the E1-deleted region, and in order to further reduce the expression of E4orf6, a vector in which the Kozak sequence in front of the rearranged E4orf6 gene in the E4re #13 vector was removed was constructed.

TABLE 5

| Abbreviation | Full name | SEQ. ID. NO |
|---|---|---|
| E4re#27 | Adk35F2-Spike/E4orf6(RSV)-E4dl-711 | SEQ. ID. NO: 29 |
| E4re#28 | Adk35RF-Spike/E4orf6(RSV)-E4dl-711 | SEQ. ID. NO: 30 |

TABLE 5-continued

| Abbreviation | Full name | SEQ. ID. NO |
|---|---|---|
| E4re#29 | Adk35F2-Spike/E4orf6(mPGK)-E4dl-711 | SEQ. ID. NO: 31 |
| E4re#30 | Adk35F2-Spike/E4orf6(CMV)-E4dl-711 | SEQ. ID. NO: 32 |
| E4re#31 | Adk35RF-Spike/E4orf6(mPGK)-E4dl-711 | SEQ. ID. NO: 33 |
| E4re#32 | Adk35F2-Spike/E4orf6(mPGK)-E4dl-12 | SEQ. ID. NO: 34 |
| E4re#33 | Adk35F2-Spike/E4orf6(mPGK)-E4dl-27 | SEQ. ID. NO: 35 |
| E4re#34 | Adk35F2-Spike/E4orf6(mPGK)-E4dl-42 | SEQ. ID. NO: 36 |
| E4re#35 | Adk35F2-Spike/E4orf6(mPGK)-E4dl-57 | SEQ. ID. NO: 37 |
| E4re#36 | Adk35F2-Spike/E4orf6(mPGK)-E4dl-318 | SEQ. ID. NO: 38 |
| E4re#37 | Adk35F2-Spike/E4orf6(mPGK)-E4dl-421 | SEQ. ID. NO: 39 |
| E4re#38 | Adk35F2-S04/E4O6(mPGK)(no kozak)-E4dl-355 | SEQ. ID. NO: 40 |
| E4re#39 | Adk35RF-Spike/E4orf6(RSV)-E4dl-12 | SEQ. ID. NO: 41 |
| E4re#40 | Adk35RF-Spike/E4orf6(RSV)-E4dl-27 | SEQ. ID. NO: 42 |
| E4re#41 | Adk35RF-Spike/E4orf6(RSV)-E4dl-42 | SEQ. ID. NO: 43 |
| E4re#42 | Adk35RF-Spike/E4orf6(RSV)-E4dl-57 | SEQ. ID. NO: 44 |
| E4re#43 | Adk35RF-Spike/E4orf6(RSV)-E4dl-318 | SEQ. ID. NO: 45 |
| E4re#44 | Adk35RF-Spike/E4orf6(RSV)-E4dl-421 | SEQ. ID. NO: 46 |

Example 8: Verification of Adenovirus Productivity

To verify the mature adenovirus productivity of the E4re #13, 14, 19, 20 and 29 vectors, adenovirus was produced at CellSTACK 10 (CS10) scale, purified with cesium chloride (CsCl), and then 293R cells were re-infected with the virus at 500 vp/cell at CS10 scale. The cells were harvested, disrupted, purified, and adenovirus was purified by FPLC, and the virus particle content was measured by HPLC to confirm the productivity of the virus stock solution.

As a result, it was confirmed that the vectors with rearranged E4 exhibited 73% to 98% of the productivity of the control vector.

TABLE 6

| Sample | Control vector | E4re#13 | E4re#14 | E4re#20 | E4re#19 | E4re#29-1 | E4re#29-2 |
|---|---|---|---|---|---|---|---|
| Unit content (VP/CS10) | 3.03E+13 | 3.55E+13 | 3.24E+13 | 2.59E+13 | 3.05E+13 | 2.41E+13 | 2.01E+13 | 2.25E+13 |
| Productivity | 100% | 98% | 79% | 93% | 73% | 61% | 68% |

Example 9: Verification of Replication Competent Adenovirus Appearance by E4re #29 Adenoviral Vector A cell-based RCA negative test was performed with the E4re #29 adenoviral vector. After infecting 36 T175 flasks of A549 cells with 4.14E+10 VP, the cells were harvested and reinfection was repeated 4 times. One week after the last infection, the cytopathic effect was confirmed under a microscope.

As a result, as shown in FIG. 11, replication competent adenovirus (RCA) was not detected in all the 36 flasks.

The E4re #29 adenoviral vector was subcultured in the HEK293R production cell line to obtain passage 4, passage 5, and passage 6 viruses. A549 cells were infected with each passage virus at 3E+10 VP, and viral DNA was extracted after 10 days. The presence or absence of replication competent adenovirus was confirmed by quantitative PCR using E1 gene-specific primers.

Figure 12:
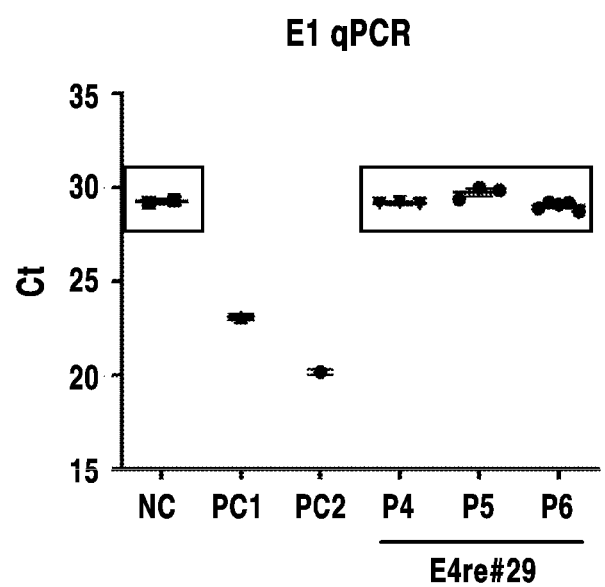
FIG. 12 is a diagram confirming whether RCA was detected according to passage increase of the E4re #29 adenoviral vector.

As a result, as shown in FIG. 12, it was confirmed that RCA was not detected even when the virus passage increased.

Example 10: Comparison of Intracellular Degree of Antigen Expression of Vectors with Rearranged E4

In order to compare the productivity, degree of spike protein antigen expression, and immunogenicity of the final four vectors (E4re #13, 14, 19, 20 and 29), passage 2 viruses were produced, isolated, and purified at CellSTACK 10 (CS10) scale. Cesium chloride (CsCl) density gradient centrifugation was used as a purification method, purification was performed over the first (1.2 g/ml CsCl+1.4 g/ml CsCl, 32,000 RPM, 90 minutes) and second (1.35 g/ml CsCl, 32,000 RPM, 18 hours) rounds, and complete adenoviruses were produced through dialysis (20 mM Tris-HCl, 25 mM sodium chloride, 2.5% glycerol).

To compare the intracellular degree of antigen expression by the E4re #1, 13, 14, 19, 20 and 29 vectors, the degree of antigen expression in the A549 cell line was measured by flow cytometry (FACS).

Specifically, for flow cytometry, A549 cells were distributed in a 96-well culture dish at the density of $2.5 \times 10^5$ cells per well, and then each vector and the control CLA-04 vector were inoculated into the cells at 500, 1000 or 2000 vp/cell. Then, the cells were cultured for 24 hours. Thereafter, the cells in each well were transferred to each 1.5 ml tube, and 500 μl of FACS buffer was added to each tube and centrifuged (5000 rpm, 3 minutes, 4° C.). After removing the supernatant, 50 μl of viability indicator dye (eFluor™ 450, ebioscience, cat #:65-0863-14) diluted 1:1000 was added to each tube, and surface staining was performed at 4° C. for 30 minutes.

To detect the antigens expressed inside the cells, the cell fixation/permeation concentrate (ebioscience, Cat. #: 00-5123-43) was diluted 1:4 in the cell fixation/permeation diluent (ebioscience, Cat. #: 00-5223-56), and 100 μl of the solution was added to each tube, followed by cell fixation/permeation at 4° C. for 30 minutes. Spike antigen staining was performed with a solution (antibody conc.: 0.4 μg/ml) of SARS-COV-2 spike protein antibody (GeneTex, Cat. #: GTX632604) diluted 1:2500 in a permeation buffer (ebioscience, Cat. #: 00-8333-56) at 4° C. for 1 hour, and washed. Then antigen staining was performed with a solution (antibody conc.: 2 μg/ml) of APC Goat anti-mouse IgG antibody (Biolegend, Cat: 405308), a secondary antibody, diluted 1:100 at 4° C. for 30 minutes. After the staining reaction, 300 μl of buffer was added to each sample and the degree of antigen expression was measured by flow cytometry (BD bioscience, LSRFORESSA).

the sample was analyzed at a wavelength of 450 nm with a microreader.

As a result, as shown in FIGS. 14A to 14H, it was confirmed that the amount of antibody production by the vectors #1, 13, 14, 20 and 29 was equal to that of the control vector, CLA-04.

SEQUENCE LISTING

The patent contains a lengthy sequence listing. A copy of the sequence listing is available in electronic form from the USPTO web site (https://seqdata.uspto.gov/?pageRequest=docDetail&DocID=US12098384B2). An electronic copy of the sequence listing will also be available from the USPTO upon request and payment of the fee set forth in 37 CFR 1.19(b)(3).

Figure 13A:
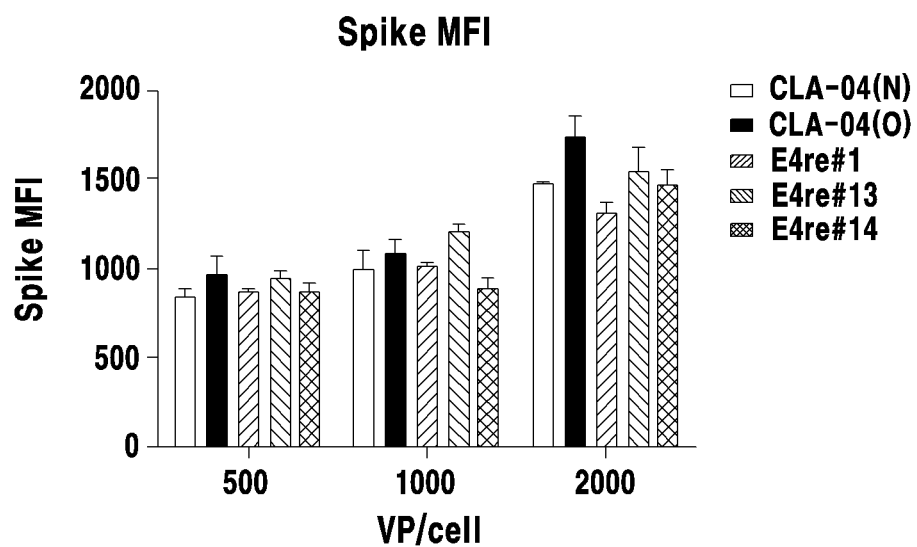
FIG. 13A is a diagram showing the degrees of antigen expression measured in the E4re #1, 13 and 14 vectors.
Figure 13B:
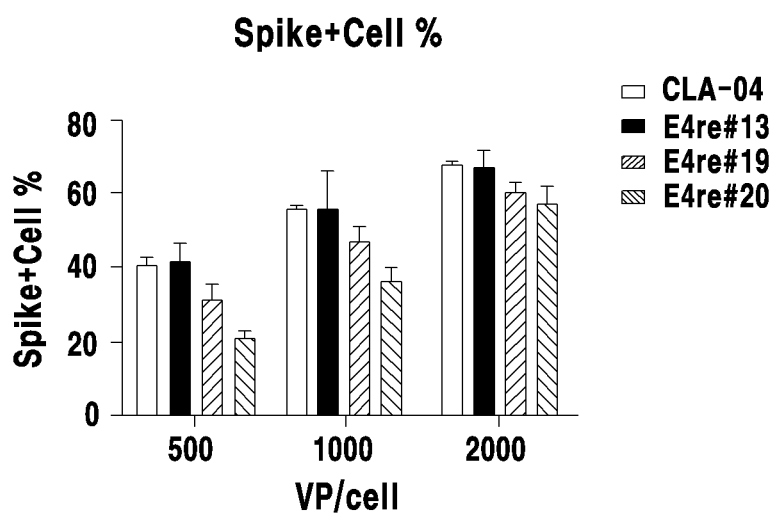
FIG. 13B is a diagram showing the degrees of antigen expression measured in the E4re #13, 19 and 20 vectors.
Figure 13C:
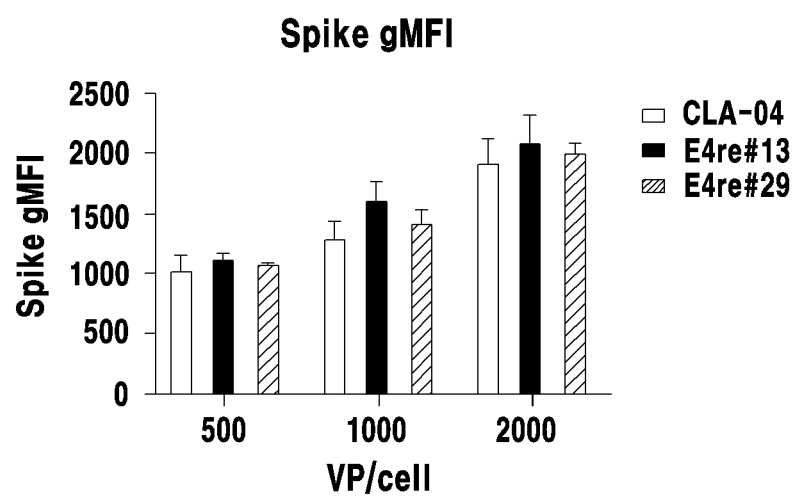
FIG. 13C is a diagram showing the degrees of antigen expression measured in the E4re #13 and 29 vectors.
Figure 14A:
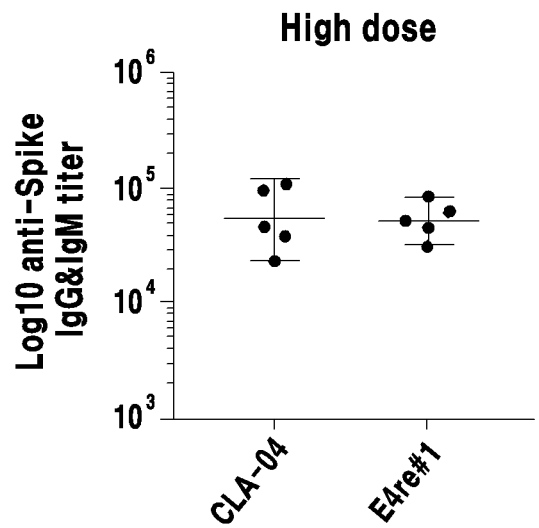
FIGS. 14A and 14B are a diagram showing the neutralizing antibody production amount in the E4re #1 vector.
Figure 14B:
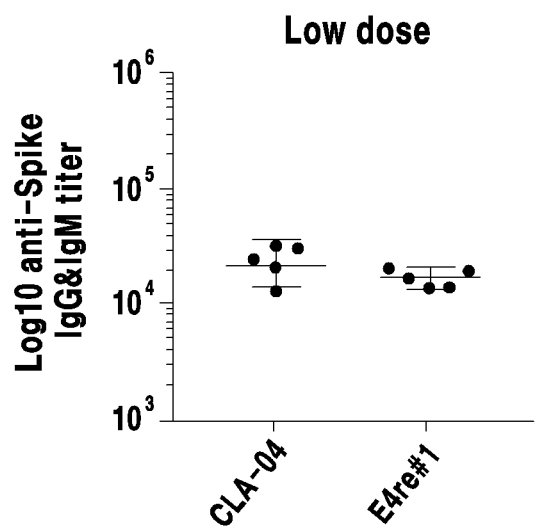
Figure 14C:
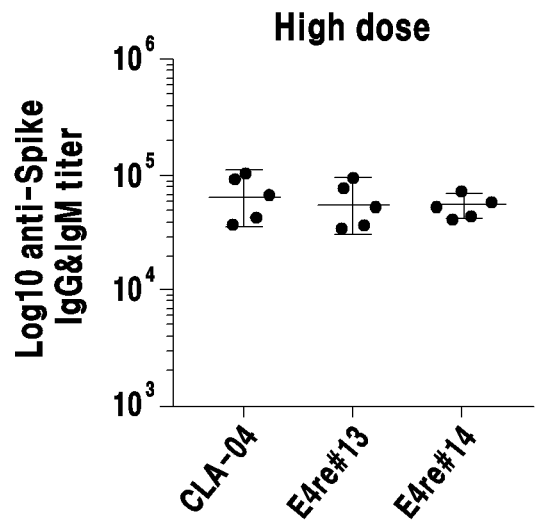
FIGS. 14C and 14D are a diagram showing the neutralizing antibody production amount in the E4re #13 and 14 vectors.
Figure 14D:
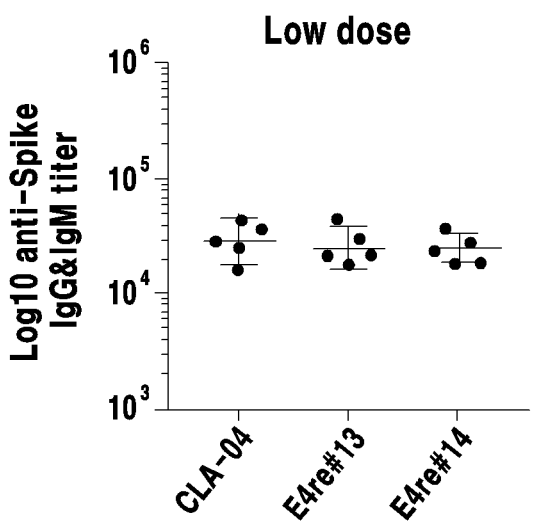
Figure 14E:
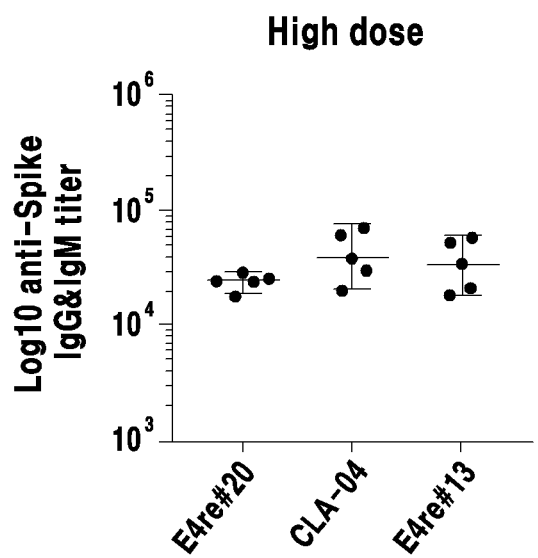
FIGS. 14E and 14F are a diagram showing the neutralizing antibody production amount in the E4re #13 and 20 vectors.
Figure 14F:
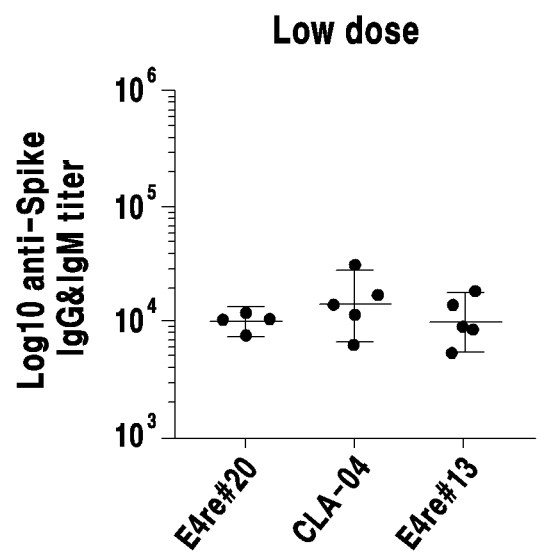
Figure 14G:
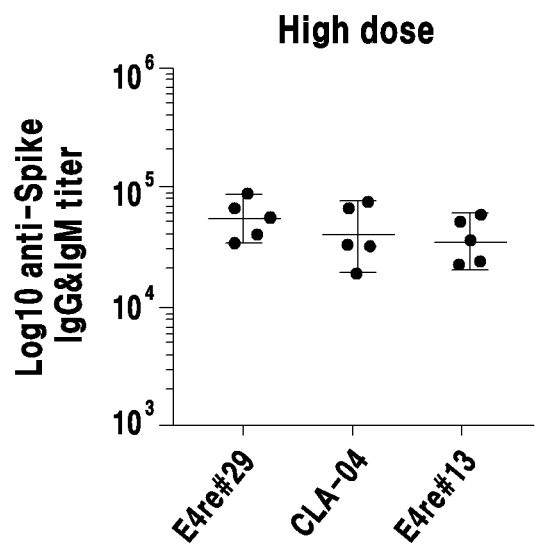
FIGS. 14G and 14H are a diagram showing the neutralizing antibody production amount in the E4re #13 and 29 vectors.
Figure 14H:
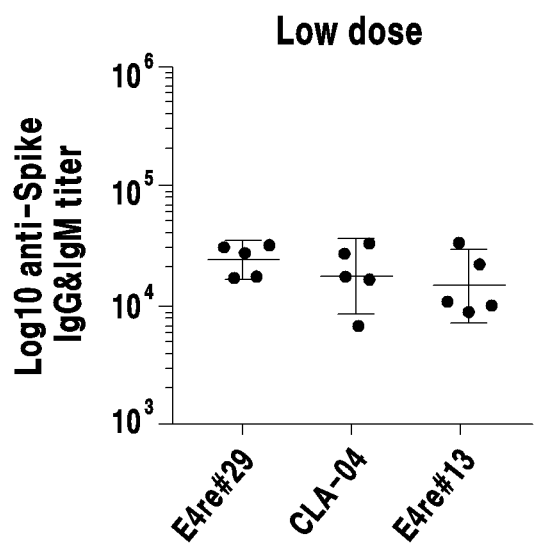

As a result, as shown in FIGS. 13a to 13c, it was confirmed that the E4re #13 and E4re #29 vectors showed the highest degree of antigen expression, which is the ability to produce proteins.

Example 11: Comparison of Neutralizing Antibody Production by Vectors with Rearranged E4

E4re #1, 13, 14, 20 and 29 vectors were intramuscularly injected into 6- to 7-week-old BALB/c mice, six mice per group. Approximately 300 μl of blood samples were collected by orbital blood sampling from mice at 2-3 weeks after administration. Then, plasma was separated by centrifugation (8000 rpm, 10 minutes, 20° C.), and the amount of neutralizing antibodies present in the blood was measured by enzyme-linked immunosorbent assay (ELISA).

Particularly, for the enzyme-linked immunosorbent assay, a spike protein (Acro Biosystems, Cat. #: SPN-C52H84) was dissolved in PBSN (PBS 1 L+Sodium Azide 0.01 g) and coated on a 96-well plate (100 ng/well), followed by reaction at 4° C. for 16 hours. After 16 hours of coating the 96-well plate, the coating protein was removed, washed three times with PBS, and then 150 μl of blocking buffer (PBSN+BSA 1%) was added to each well, followed by reaction at 37° C. for 90 minutes. During the reaction, plasma was diluted 6400-fold in dilution buffer (PBSN+ 0.1% BSA+0.05% Tween-20), and after the blocking reaction was completed, the plate was washed three times with PBS, and then 50 μl of the diluted plasma sample was added to each well, followed by reaction at 37° C. for 3 hours. Upon completion of the reaction, the plate was washed three times with PBS. The secondary antibodies GAM-IgG-HRP (southernbiotech, Cat. #: 1030-05) and GAM-IgM-HRP (southernbiotech, Cat. #: 1020-05) were diluted 1000-fold in dilution buffer and added to the plate (50 μl/well), followed by reaction at 37° C. for 2 hours. Then, the secondary antibodies were removed from the plate, the plate was washed five times with PBS, and a chromogenic reagent (TMB Peroxidase Substrate buffer, ROCKLAND, Cat. #: TMBE-1000) was added to the plate (50 μl/well), followed by color development for 15 minutes. The color development was terminated by adding 0.25 N HCl (50 μl/well), and

What is claimed is:

1. A recombinant E1/E3/E4-deleted adenoviral vector, comprising:
    an E1 gene deletion;
    an E3 gene deletion;
    an E4 gene deletion; and
    an E4 gene insertion in the E1 gene-deleted region of the adenoviral vector,
    wherein the E4 gene deletion comprises a partial or entire deletion of E4 open reading frame 6 (E4orf6), wherein the deletion is 10 to 1,500 bp in length; and
    wherein the E4 gene insertion comprises insertion of E4orf6, and is expressed in a forward direction.

2. The recombinant adenoviral vector according to claim 1, wherein the adenoviral vector is Ad2, Ad4, Ad5, Ad11, Ad26, Ad35, Ad5/35, ChAd68, FAd9 or PAd3 vector.

3. The recombinant adenoviral vector according to claim 1, wherein the E4 gene deletion further comprises a deletion of E4 open reading frame 6/7 (E4orf6/7) and/or a deletion of E4 open reading frame 4 (E4orf4).

4. The recombinant adenoviral vector according to claim 1, wherein the E4orf6 in the E4 gene insertion does not comprise a kozak sequence.

5. The recombinant adenoviral vector according to claim 1, wherein the vector further comprises a sequence encoding an antigen protein inserted in the E1 gene-deleted region.

6. The recombinant adenoviral vector according to claim 5, wherein the sequence encoding the antigen protein is inserted at the 5' position of the E4 gene insertion.

7. The recombinant adenoviral vector according to claim 1, wherein the E4 gene insertion is expressed by a promoter selected from EF-1a, mPGK, RSV, cytomegalovirus (CMV), −0.25 kb of E4orf6, −0.5 kb of E4orf6, or −1.0 kb of E4orf6.

8. The recombinant adenoviral vector according to claim 5, wherein the sequence encoding the antigen protein is expressed by a cytomegalovirus (CMV) promoter.

9. A vaccine for preventing coronavirus infection, comprising the recombinant adenoviral vector of claim 1, wherein the vector further comprises a sequence encoding a coronavirus spike protein.

10. The vaccine according to claim 9, wherein the coronavirus is SARS-CoV, MERS-COV or SARS-COV-2.

11. The vaccine according to claim 9, wherein the spike protein is a recombinant spike protein in which a cleavage recognition sequence between S1 and S2 of the spike protein is replaced with a linker sequence.

12. The vaccine according to claim 11, wherein the linker sequence comprises (GGGGS)n (SEQ ID NO: 47).

13. The vaccine according to claim 12, wherein the n is an integer of 1 to 5.

14. The recombinant adenoviral vector according to claim 1, wherein the E4 gene insertion is a deleted region of the E4 gene deletion.

* * * * *